United States Patent [19]

Mao et al.

[11] Patent Number: 4,954,528

[45] Date of Patent: * Sep. 4, 1990

[54] HYPOCHOLESTEROLEMIC USE OF BIS(3,5-DI-TERTIARY-BUTLY-4-HYDROXY-PHENYLTHIO)METHANE

[75] Inventors: Simon J. T. Mao, Loveland; Richard L. Jackson, Cincinnati, both of Ohio

[73] Assignee: Merrell Dow Pharmaceuticals Inc., Cincinnati, Ohio

[*] Notice: The portion of the term of this patent subsequent to Feb. 13, 2007 has been disclaimed.

[21] Appl. No.: 433,985

[22] Filed: Nov. 15, 1989

Related U.S. Application Data

[63] Continuation-in-part of Ser. No. 281,433, Dec. 8, 1988, Pat. No. 4,900,757.

[51] Int. Cl.$^5$ ............................................. A61K 31/10
[52] U.S. Cl. .................................. 514/712; 514/824
[58] Field of Search ................................ 514/712, 824

[56] References Cited

U.S. PATENT DOCUMENTS 3,576,883  4/1971  Neuworth ............................ 514/712
3,862,332  1/1975  Barnhart et al. ..................... 514/712

FOREIGN PATENT DOCUMENTS 1199871  7/1970  United Kingdom .

OTHER PUBLICATIONS

M. S. Brown, J. L. Goldstein, Ann. Rev. Biochem, 52,223–261 (1983).
G. L. Miller, M.D., Ann. Rev. Med, 31, 97–108 (1980).
J. G. Patton, et al., Clin. Chem., 29, 1898–1903 (1983).
S. J. T. Mao, et al., Clin. Chem., 29, 1890–1897 (1983).
S. Parthasarathy, et al., J. Clin. Invest. 77 641–644 (1986).
T. Kita, et al., Proc. Natl. Acad. Sci USA 84, 5928–5931 (1987).
T. E. Carew, et al., Proc. Natl. Acad. Sci. USA 84, 7725–7729 (1987).
Y. Watanabe, Atherosclerosis, 36, 261–268 (1980).
Product Labeling for Lorelco®, Physician's Desk Reference, 42nd edition, (1988), Medical Economics Co., Inc., Oradell, N.J.

*Primary Examiner*—Douglas W. Robinson
*Assistant Examiner*—Raymond J. Henley, III
*Attorney, Agent, or Firm*—Louis J. Wille

[57] ABSTRACT

The present invention relates to a method of lowering total serum cholesterol in a patient in need thereof comprising administering to said patient a therapeutically effective hypocholesterolemic amount of bis(3,5-di-tertiary-butyl-4-hydroxyphenylthio)methane.

2 Claims, No Drawings

HYPOCHOLESTEROLEMIC USE OF BIS(3,5-DI-TERTIARY-BUTLY-4-HYDROXY-PHENYLTHIO)METHANE

This is a continuation in part of Ser. No. 07/281,433, filed December 8, 1988 now U.S. Pat. No. 4,900,757.

Atherosclerosis as manifested in its major clinical complication, ischaemic heart disease, continues to be a major cause of death in industrialized countries. It is now well accepted that atherosclerosis can begin with local injury to the arterial endothelium followed by proliferation of arterial smooth muscle cells from the medial layer to the intimal layer along with deposition of lipid and accumulation of foam cells in the lesion. As the atherosclerotic plaque develops it progressively occludes more and more of the affected blood vessel and can eventually lead to ischaemia or infarction. Therefore, it is desirable to provide methods of inhibiting the progression of atherosclerosis in patients in need thereof.

There is now a large body of evidence demonstrating that hypercholesterolemia is an important risk factor associated with heart disease. For example, in December 1984, a National Institute of Health Consensus Development Conference Panel concluded that lowering definitely elevated blood cholesterol levels (specifically blood levels of low-density lipoprotein cholesterol) will reduce the risk of heart attacks due to coronary heart disease. Accordingly, it is desirable to provide a method for reducing plasma cholesterol in patients with hypercholesterolemia.

Typically, cholesterol is carried in the blood of warm-blooded animals in certain lipid-protein complexes such as chylomicrons, very low density lipoprotein (VLDL), low density lipoprotein (LDL), and high density lipoprotein (HDL). It is widely accepted that LDL functions in a way that directly results in deposition of the LDL cholesterol in the blood-vessel wall and that HDL functions in a way that results in the HDL picking up cholesterol from the vessel wall and transporting it to the liver where it is metabolized [Brown and Goldstein, Ann. REv. Biochem. 52, 223 (1983); Miller, Ann. Rev. MEd. 31, 97 (1980)]. For example, in various epidemiologic studies the LDL cholesterol levels correlate well with the risk of coronary heart disease whereas the HDL cholesterol levels are inversely associated with coronary heart disease [Patton et al., Clin. Chem. 29, 1890 (1983)]. It is generally accepted by those skilled in the art that reduction of abnormally high LDL cholesterol levels is effective therapy not only in the treatment of hypercholesterolemia but also in the treatment of atherosclerosis. Accordingly, it is desirable to provide a method for reducing LDL cholesterol in patients with hypercholesterolemia.

Furthermore, there is evidence based on animal and laboratory findings that peroxidation of LDL facilitates the accumulation of cholesterol in monocyte/macrophages which eventually are transformed into foam cells and become deposited in the sub-endothelial space of the vessel wall. The accumulation of foam cells in the vessel wall is recognized as an early event in the formation of an atherosclerotic plaque. Thus it is believed that peroxidation of LDL is an important prerequisite to the facilitated accumulation of cholesterol in the vessel wall and the subsequent formation of an atherosclerotic plaque. For example, it has been shown that monocyte/macrophages take up and degrade native LDL at relatively low rates and without marked accumulation of cholesterol. In contrast, oxidized LDL is taken up by these monocyte/macrophages at much higher rates and with marked accumulation of cholesterol [Parthasarathy et al., J. Clin. Invest. 77, 641 (1986)].

It has been shown that 2,2'-bis(3,5-di-tertiary-butyl-4hydroxyphenylthio)propane (also known as probucol), which is a known antioxidant, may prevent the progression of atherosclerosis in a manner which is independent of its effect on lowering plasma cholesterol levels [See Kita et al. Proc. Natl. Acad. Sci. USA 84, 5298, (1987); Carew et al., Proc. Natl. Acad. Sci. USA 84, 7725, (1987)]. It is believed that antioxidants, such as probucol, may prevent or inhibit the development of atherosclerosis by inhibiting the peroxidation of LDL and thus preventing the facilitated accumulation of cholesterol in monocyte/macrophages which eventually are transformed into foam cells and become deposited in the sub-endothelial space of the vessel wall [See Parthasarathy et al. J. Clin. Invest. 77, 641 (1986)]. Accordingly, it is desirable to provide a method of inhibiting the peroxidation of LDL.

Barnhart and Shea in U.S. Pat. No. 3,862,332 disclosed that 2,2'-bis(3,5-di-tertiary-butyl-4hydroxyphenylthio)propane, also known as probucol, and 1,1'bis(3,5-di-tertiary-butyl-4-hydroxyphenylthio)ethane are useful in lowering serum cholesterol in animals. Probucol is currently approved for administration to man by the U.S. Food and Drug Administration as a pharmaceutical agent indicated for the reduction of elevated serum cholesterol in patients with primary hypercholesterolemia (elevated LDL) who have not responded adequately to diet, weight reduction and control of diabetes mellitus (See 'Physician's Desk Reference', 42nd Edition, 1988, Medical Economics Company, Inc., Oradell, N.J. 07649). In British Patent Specification No. 1,199,871, probucol was disclosed as providing a 59% reduction in the blood cholesterol of mice after a 2 week treatment. However, in that same reference, it was disclosed that the compound involved in the method of use of the present invention, i.e., bis(3,5-di-tertiary-butyl-4-hydroxyphenylthio)methane, provided no reduction in the blood cholesterol of mice after comparable treatment. Surprisingly, bis(3,5-di-tertiary-butyl-4-hydroxyphenylthio)methane has now been found to be effective in lowering total serum cholesterol, in lowering LDL cholesterol, in inhibiting peroxidation of LDL and in inhibiting the progression of atherosclerosis in patients in need thereof.

For example, bis(3,5-di-tertiary-butyl-4hydroxyphenylthio)methane reduces serum cholesterol and prevents the progression of atherosclerosis in the Watanabe heritable hyperlipidemic (WHHL) rabbit. The WHHL rabbit is a strain of rabbit with a consistently inherited hyperlipidemic trait. Because these animals lack LDL receptors, they have abnormally elevated concentrations of serum cholesterol and spontaneous development of aortic atherosclerosis [see Watanabe, Atherosclerosis 36, 261 (1980)]. WHHL rabbits are well recognized as an animal model for human familial hypercholesterolemia and it has previously been shown [Kita et al., Proc. Natl. Acad. Sci. USA 84, 5928 (1987); Carew et al., Proc. Natl. Acad. Sci USA 84, 7725 (1987)]that probucol is effective in preventing the progression of atherosclerosis in this model.

In addition, Parthasarathy et al.[J. Clin. Invest. 77, 641 (1986)]showed that probucol inhibits the oxidative modification of LDL by cupric ions in vitro and by endothelial cells in vivo. Kita et al. [*Proc. Natl. Acad. Sci. USA* 84, at 5931]thus theorize that probucol might inhibit atherosclerosis in the WHHL rabbit 'by limiting oxidative modification of LDL and subsequently by limiting foam cell transformation of macrophages in vivo'.

The present invention relates to the use of bis(3,5-ditertiary-butyl-4-hydroxyphenylthio)methane in treating atherosclerosis and/or hypercholesterolemia in patients suffering therefrom.

More specifically, the present invention provides a method of lowering total serum cholesterol and of lowering LDL cholesterol in a patient in need thereof comprising administering to said patient a therapeutically effective hypocholesterolemic amount of bis(3,5-di-tertiary-butyl-4hydroxyphenylthio)methane. The present invention also provides a method of inhibiting the progression of atherosclerosis in a patient in need thereof comprising administering to said patient a therapeutically effective antiatherosclerotic amount of bis(3,5-di-tertiary-butyl-4hydroxyphenylthio)methane. Finally, the present invention provides a method of inhibiting the peroxidation of LDL in a patient in need thereof comprising administering to said patient a therapeutically effective antioxidant amount of bis(3,5-di-tertiary-butyl-4-hydroxyphenylthio)methane.

As used herein, the term 'patient' refers to warmblooded animals or mammals, including WHHL rabbits and humans but not including rodents, who are in need of treatment for atherosclerosis or hypercholesterolemia, such as, for example, in the case of a patient suffering from familial hyperlipidemia.

Hypercholesterolemia is a disease state characterized by levels of serum cholesterol or of LDL cholesterol which are elevated by a clincially signifiant amount over that considered normal by those of ordinary skill in the art. The identification of those patients who are in need of treatment for hypercholesterolemia is well within the ability and knowledge of one skilled in the art. For example, individuals who have serum cholesterol levels or LDL cholesterol levels, as determined by clinical laboratory tests, which are substantially and chronically elevated over that considered normal by those of ordinary skill in the art, are patients in need of treatment for hypercholesterolemia. By way of further example, individuals who are at risk of developing hypercholesterolemia can also be patients in need of treatment for hypercholesterolemia. A clinician skilled in the art can readily identify, by the use of clinical tests, physical examination and medical/family history, those patients who are suffering from hypercholesterolemia and those who are at risk of developing hypercholesterolemia and thus readily determine if an individual is a patient in need of treatment for hypercholesterolemia.

An effective hypocholesterolemic amount of bis(3,5-ditertiary-butyl-4-hydroxyphenylthio)methane is an amount which is effective in reducing serum cholesterol levels or LDL cholesterol levels in a patient in need thereof. As such, successful treatment of a patient for hypercholesterolemia is understood to include reducing a patient's serum cholesterol or LDL cholesterol levels. Successful treatment for hypercholesterolemia is also understood to include prophylaxis in preventing clinically significant elevations in serum cholesterol or in LDL cholesterol levels in a patient who is at risk of the development of hypercholesterolemia.

Atherosclerosis is a disease state characterized by the development and growth of atherosclerotic lesions or plaque. The identification of those patients who are in need of treatment for atherosclerosis is well within the ability and knowledge of one skilled in the art. For example, individuals who are either suffering from clinically significant atherosclerosis or who are at risk of developing clinically significant atherosclerosis are patients in need of treatment for atherosclerosis. A clinician skilled in the art can readily determine, by the use of clinical tests, physical examination and medical/family history, if an individual is a patient in need of treatment for atherosclerosis.

An effective antiatherosclerotic amount of bis(3,5-ditertiary-butyl-4-hydroxyphenylthio)methane is an amount which is effective in inhibiting development or growth of atherosclerosis in a patient in need thereof. As such, successful treatment of a patient for atherosclerosis is understood to include effectively slowing, interrupting, arresting, or stopping atherosclerotic lesion or plaque development or growth and does not necessarily indicate a total elimination of the atherosclerosis. It is further understood and appreciated by those skilled in the art that successful treatment for atherosclerosis can include prophylaxis in preventing atherosclerotic lesion or plaque formation.

It is believed that peroxidation of LDL facilitates the deposition of cholesterol in macrophages which subsequently are deposited in the vessel wall and are transformed into foam cells. The identification of those patients who are in need of inhibition of peroxidation of LDL is well within the ability and knowledge of one skilled in the art. For example, those individuals who are in need of treatment for atherosclerosis as defined hereinabove, are also patients who are in need of inhibition of peroxidation of LDL. Furthermore, an effective antioxidant amount of bis(3,5-di- tertiary-butyl-4-hydroxyphenylthio)methane is an amount which is effective in inhibiting the peroxidation of LDL in the patient's blood.

An effective antiatherosclerotic, antioxidant or hypocholesterolemic dose can be readily determined by the use of conventional techniques and by observing results obtained under analogous circumstances. In determining the effective dose, a number of factors are considered including, but not limited to: the species of patient; its size, age, and general health; the specific disease involved; the degree of or involvement or the severity of the disease; the response of the individual patient; the particular compound administered; the mode of administration; the bioavailability characteristics of the preparation administered; the dose regimen selected; and the use of concomitant medication.

An effective antiatherosclerotic, antioxidant or hypocholesterolemic amount of bis(3,5-di-tertiary-butyl-4hydroxyphenylthio)methane will generally vary from about 1 milligram per kilogram of body weight per day (mg/kg/day) to about 5 grams per kilogram of body weight per day (gm/kg/day). A daily dose of from about 1 mg/kg to about 500 mg/kg is preferred.

In effecting treatment of a patient, bis(3,5-di- tertiary-butyl-4-hydroxyphenylthio)methane can be administered in any form or mode which makes the compound bioavailable in effective amounts, including oral and parenteral routes. For example, the compound can be administered orally, subcutaneously, intramuscularly, intravenously, transdermally, intranasally, rectally, and the like. Oral administration is generally preferred. One skilled in the art of preparing formulations can readily select the proper form and mode of administration depending upon the disease state to be treated, the stage of the disease, and other relevant circumstances.

Bis(3,5-di-tertiary-butyl-4-hydroxyphenylthio)methane can be administered in the form of pharmaceutical compositions or medicaments which are made by combining bis(3,5-di-tertiary-butyl-4-hydroxyphenylthio)methane with pharmaceutically acceptable carriers or excipients, the proportion and nature of which are determined by the chosen route of administration, and standard pharmaceutical practice.

The pharmaceutical compositions or medicaments are prepared in a manner well known in the pharmaceutical art. The carrier or excipient may be a solid, semisolid, or liquid material which can serve as a vehicle or medium for the active ingredient. Suitable carriers or excipients are well known in the art. The pharmaceutical composition may be adapted for oral or parenteral use and may be administered to the patient in the form of tablets, capsules, suppositories, solution, suspensions, or the like.

The pharmaceutical compositions may be administered orally, for example, with an inert diluent or with an edible carrier. They may be enclosed in gelatin capsules or compressed into tablets. For the purpose of oral therapeutic administration, bis(3,5-di-tertiary-butyl-4-0. hydroxyphenylthio)methane may be incorporated with excipients and used in the form of tablets, troches, capsules, elixirs, suspensions, syrups, wafers, chewing gums and the like. These preparations should contain at least 4% of bis(3,5-di-tertiary-butyl-4-hydroxyphenylthio)methane, the active ingredient, but may be varied depending upon the particular form and may conveniently be between 4% to about 70% of the weight of the unit. The amount of the active ingredient present in compositions is such that a unit dosage form suitable for administration will be obtained.

The tablets, pills, capsules, troches and the like may also contain one or more of the following adjuvants: binders, such as microcrystalline cellulose, gum tragacanth or gelatin; excipients, such as starch or lactose, disintegrating agents such as alginic acid, Primogel, corn starch and the like; lubricants, such as magnesium stearate or Sterotex; glidants, such as colloidal silicon dioxide; and sweetening agents, such as sucrose or saccharin may be added or flavoring agents, such as peppermint, methyl salicylate or orange flavoring. When the dosage unit form is a capsule, it may contain, in addition to materials of the above type, a liquid carrier such as polyethylene glycol or a fatty oil. Other dosage unit forms may contain other various materials which modify the physical form of the dosage unit, for example, as coatings. Thus, tablets or pills may be coated with sugar, shellac, or other enteric coating agents. A syrup may contain, in addition to the active ingredient, sucrose as a sweetening agent and certain preservatives, dyes and colorings and flavors. Materials used in preparing these various compositions should be pharmaceutically pure and non-toxic in the amounts used.

For the purpose of parenteral administration, bis(3,5-di-tertiary-butyl-4-hydroxyphenylthio)methane may be incorporated into a solution or suspension. These preparations should contain at least 0.1% of a compound of the invention, but may be varied to be between 0.1 and about 50% of the weight thereof. The amount of the active ingredient present in such compositions is such that a suitable dosage will be obtained.

The solutions or suspensions may also include one or more of the following adjuvants: sterile diluents such as water for injection, saline solution, fixed oils, polyethylene glycols, glycerine, propylene glycol or other synthetic solvents; antibacterial agents such as benzyl alcohol or methyl paraben; antioxidants such as ascorbic acid or sodium bisulfite; chelating agents such as ethylene diaminetetraacetic acid; buffers such as acetates, citrates or phosphates and agents for the adjustment of toxicity such as sodium chloride or dextrose. The parenteral preparation can be enclosed in ampules, disposable syringes or multiple dose vials made of glass or plastic.

Bis(3,5-di-tertiary-butyl-4-hydroxyphenylthio)methane can be prepared by methods well known and appreciated by those of ordinary skill in the art. For example, the compound can be prepared by treating 2,6-di-tertiary-butyl4-mercaptophenol with 1,3,5-trioxane in the presence of acetonitrile and DOWEX 50 resin under reflux conditions. 2,6-Di-tertiary-butyl-4-mercaptophenol can be prepared as described, for example, by Krauss in U.S. Pat. No. 4,734,527.

The following examples illustrate the preparation and use of bis(3,5-di-tertiary-butyl-4-hydroxyphenylthio)methane according to the present invention. These examples are illustrative only and are not intended to limit the scope of the invention in any way.

EXAMPLE 1

Preparation of Bis(3,5-di-tertiary-butyl-4hydroxyphenylthio)methane

Combine acetonitrile [1800 milliliters (ml)], 1,3,5trioxane [71.0 grams (gm), 0.79 moles (mol)], 2,6-ditertiary-butyl-4-mercaptophenol [678.4 gm, 2.85 mol]and 2.5 gm DOWEX 50 resin in a three-necked flask with a thermowell. Bring the mixture to reflux under a nitrogen 5 atmosphere and maintain for 36–48 hours to provide the title compound.

Filter the mixture to remove the DOWEX 50 resin and concentrate the filtrate in vacuo to give an amber oil. Dissolve the oil in 1 liter of ethanol at 70 degrees Celsius (°C.) and add 125 ml of water. Allow the mixture to cool to ambient temperature over night while stirring. Collect the resulting crystalline product by filtration and wash the filter cake with 75 ml of cold ethanol/water (90/10). Recrystallize the product from ethanol/water and collect by filtration Wash the filter cake with 50 ml of cold ethanol and dry the product in a vacuum oven at 50° C and 15 mm Hg overnight to yield 406.9 gm of the purified title compound as a white solid. Melting point 94-95° C. Elemental analysis:

30 Calculated—C=71.3%, H=9.07%;
Found—C=71.3%, H=9.09%.

EXAMPLE 2

Inhibition of LDL Peroxidation

Determine the degree of inhibition of LDL peroxidation by probucol and bis(3,5-di-tertiary-butyl-4-hydroxyphenylthio)methane by the method of Yagi et al. [*Vitamins* 39, 105 (1968)]. Incubate a 0.5 ml solution containing 250 micrograms ($\mu$g) of LDL with either probucol or bis(3,5-di-tertiary-butyl-4hydroxyphenylthio)methane, in amounts varying from 0 to 30 $\mu$g, for 30 minutes at 42° C. To this mixture add 1 ml of a 0 cupric sulfate solution (final concentration 12.5 $\mu$M) and incubate at 37° C. for 2.5 hours. Determine the amount of peroxidation of LDL by the thiobarbituric acid assay. Calculate the dose of probucol and bis(3,5-di-tertiarybutyl-4-hydroxyphenylthio)methane required to inhibit 50% of LDL peroxidation ($ID_5$).

As shown in Table 1, the $ID_{50}$ for probucol is 12.5 μg whereas the $ID_{50}$ for bis(3,5-di-tertiary-butyl-4-hydroxyphenylthio)methane is only 6 μg. Therefore, this data indicates that bis(3,5-di-tertiary-butyl-4-hydroxyphenylthio)methane is over twice as effective in inhibiting the peroxidation of human LDL than is probucol.

TABLE 1

Effect of Probucol and Bis(3,5-di-tertiary-butyl-4-hydroxyphenylthio)methane on LDL Peroxidation

| Treatment[a] | $ID_{50}$ |
| --- | --- |
| A | 12.5 μg |
| B | 6 μg |

[a]Treatment A = Probucol
Treatemnt B = bis(3,5-ditertiary-butyl-4-hydroxy phenylthio)methane

EXAMPLE 3

Hypocholesterolemic Effects of Bis(3,5-di-tertiarybutyl-4-hydroxyphenylthio)methane in Cholesterol-fed Rabbits New Zealand White Rabbits were separated into two groups of 4 or 5 rabbits per group. During a Pretreatment Period, one group [Control Group]was fed standard rabbit chow for 12 weeks and the other group [Treatment Group]received standard rabbit chow containing bis(3,5-di-tertiarybutyl-4-hydroxyphenylthio)methane (1% by weight) for 12 weeks. At the end of the 12 week pretreatment period, the Control Group was fed standard rabbit chow containing cholesterol (1% by weight) for 7 weeks, while the Treatment Group received standard rabbit chow containing bis (3,5-ditertiarybutyl-4-hydroxyphenylthio)methane (1% by weight) and cholesterol (1% by weight) for 7 weeks. During the Treatment Period, and specifically on days 15, 22, 35 and 49 after starting into the Treatment Period, blood samples were taken from the animals and were analyzed for plasma cholesterol by an enzymatic method using a DACOS analyzer (Coulter Electronics Inc., Hialeah, Fla., USA).

The results of treatment of cholesterol-fed rabbits with bis(3,5-di-tertiarybutyl-4-hydroxyphenylthio)methane is shown in Table 2.

TABLE 2

Hypocholesterolemic Effects of Bis(3,5-di-tertiarybutyl-4-hydroxyphenylthio)methane in Cholesterol-fed Rabbits

| GROUP | Plasma Cholesterol (mg/dl ± s.d.[c]) 15 days | Plasma Cholesterol (mg/dl ± s.d.) 22 days | Plasma Cholesterol (mg/dl ± s.d.) 35 days | Plasma Cholesterol (mg/dl ± s.d.) 49 days |
| --- | --- | --- | --- | --- |
| Control Group[a] | 1266 ± 349.2 | 1453 ± 553.4 | 1570 ± 238.5 | 1694 ± 328.3 |
| Treatment Group[b] | 636 ± 111.4 | 785.3 ± 106.7 | 1218 ± 85.9 | 1678 ± 382.5 |

[a]5 animals
[b]4 animals
[c]s.d. refers to standard deviation

The above results indicate that bis(3,5-ditertiarybutyl-4-hydroxyphenylthio)methane reduces plasma cholesterol in cholesterol-fed rabbits at least at 15 and 22 days after initiating cholesterol treatment.

What is claimed is:

1. A method of lowering total serum cholesterol in a patient in need thereof comprising administering to said patient a therapeutically effective hypocholesterolemic amount of bis(3,5-di-tertiary-butyl-4-hydroxyphenylthio) methane.

2. A method of treating a patient for hypercholesterolemia comprising administering to said patient a therapeutically effective hypocholesterolemic amount of bis(3,5-di-tertiary-butyl-4hydroxyphenylthio)methane.

* * * * *